United States Patent
Gurcan et al.

(10) Patent No.: US 10,977,794 B2
(45) Date of Patent: Apr. 13, 2021

(54) AUTOMATED IDENTIFICATION OF TUMOR BUDS

(71) Applicant: Ohio State Innovation Foundation, Columbus, OH (US)

(72) Inventors: Metin Gurcan, Winston-Salem, NC (US); Wendy Frankel, Columbus, OH (US); Wei Chen, Columbus, OH (US); Mohammad Faizal Ahmad Fauzi, Selangor (MY)

(73) Assignee: Ohio State Innovation Foundation, Columbus, OH (US)

( * ) Notice: Subject to any disclaimer, the term of this patent is extended or adjusted under 35 U.S.C. 154(b) by 52 days.

(21) Appl. No.: 16/230,118

(22) Filed: Dec. 21, 2018

(65) Prior Publication Data

US 2019/0206055 A1    Jul. 4, 2019

Related U.S. Application Data

(60) Provisional application No. 62/613,464, filed on Jan. 4, 2018.

(51) Int. Cl.
| | | |
|---|---|---|
| *G06T 7/77* | (2017.01) | |
| *G06T 7/00* | (2017.01) | |
| *G06T 7/136* | (2017.01) | |
| *G16B 5/00* | (2019.01) | |
| *G16B 40/00* | (2019.01) | |

(Continued)

(52) U.S. Cl.
CPC .......... *G06T 7/0014* (2013.01); *G06T 7/0012* (2013.01); *G06T 7/11* (2017.01); *G06T 7/136* (2017.01); *G16B 5/00* (2019.02); *G16B 40/00* (2019.02); *G16B 40/20* (2019.02); *G06T 2207/10024* (2013.01); *G06T 2207/30032* (2013.01); *G06T 2207/30096* (2013.01)

(58) Field of Classification Search
CPC ..... G06T 7/0014; G06T 7/0012; G06T 7/136; G06T 7/11; G06T 2207/10024; G06T 2207/30096; G06T 2207/30032; G16B 40/20; G16B 5/00; G16B 40/00
See application file for complete search history.

(56) References Cited

U.S. PATENT DOCUMENTS

| | | | |
|---|---|---|---|
| 2014/0236495 A1* | 8/2014 | Thiery | G16B 20/00 702/19 |
| 2017/0103521 A1* | 4/2017 | Chukka | G06T 7/0012 |

OTHER PUBLICATIONS

Rogojanu et al., "Quantitative Image Analysis of Epithelial and Stromal Area in Histological Sections of Colorectal Cancer: An Emerging Diagnostic Tool", Hindawi Publishing Corporation BioMed Research International vol. 2015, Article ID 569071 (Year: 2015).*

(Continued)

*Primary Examiner* — Qian Yang
(74) *Attorney, Agent, or Firm* — Meunier Carlin & Curfman LLC

(57) ABSTRACT

Automated image analysis methods to identify and quantify tumor buds in a high resolution image of a section of a tumor that is stained using either pan-cytokeratin AE1/3 or hematoxylin and eosin (H&E) are disclosed. The methods may be used to aid and/or replace manual visual inspection for tumor buds and may be used to predict a clinically relevant outcome or treatment in some cases. The disclosed methods may be used for many different cancer types, such as colorectal cancer.

11 Claims, 5 Drawing Sheets

(51) Int. Cl.
 G06T 7/11 (2017.01)
 G16B 40/20 (2019.01)

(56) References Cited

OTHER PUBLICATIONS

Koelzer et al., "Tumor budding in colorectal cancer revisited: results of a multicenter interobserver study", Virchows Arch (2015) 466:485-493 (Year: 2015).*
Allard et al., "Linear quantification of lymphoid infiltration of the tumor margin: a reproducible method, developed with colorectal cancer tissues, for assessing a highly variable prognostic factor", Diagnostic Pathology 2012, 7:156 (Year: 2012).*
M. Boxberg, M. Jesinghaus, C. Dorfner, C. Mogler, E. Drecoll, A. Warth, et al., "Tumour budding activity and cell nest size determine patient outcome in oral squamous cell carcinoma: proposal for an adjusted grading system," Histopathology, vol. 70, pp. 1125-1137, 2017.
P. V. Angadi, P. V. Patil, K. Hallikeri, M. Mallapur, S. Hallikerimath, and A. D. Kale, "Tumor budding is an independent prognostic factor for prediction of lymph node metastasis in oral squamous cell carcinoma," International journal of surgical pathology, vol. 23, pp. 102-110, 2015.
X. Li, B. Wei, C. Sonmez, Z. Li, and L. Peng, "High tumor budding count is associated with adverse clinicopathologic features and poor prognosis in breast carcinoma," Human Pathology, 2017, 66, 222-229.
M. Jesinghaus, M. Boxberg, B. Konukiewitz, J. Slotta-Huspenina, A. M. Schlitter, K. Steiger, et al., "A Novel Grading System Based on Tumor Budding and Cell Nest Size Is a Strong Predictor of Patient Outcome in Esophageal Squamous Cell Carcinoma," The American Journal of Surgical Pathology, vol. 41, pp. 1112-1120, 2017.
K. Che, Y. Zhao, X. Qu, Z. Pang, Y. Ni, T. Zhang, et al., "Prognostic significance of tumor budding and single cell invasion in gastric adenocarcinoma," OncoTargets and therapy, vol. 10, p. 1039, 2017.
S. Olsen, J. Linda, R. C. Fields, Y. Yan, and I. Nalbantoglu, "Tumor Budding in Intestinal Type Gastric Adenocarcinoma is Associated with Nodal Metastasis and Recurrence," Human Pathology, 2017, 68, 26-33.
B. Huang, J. Cai, X. Xu, S. Guo, and Z. Wang, "High-Grade Tumor Budding Stratifies Early-Stage Cervical Cancer with Recurrence Risk," PloS one, vol. 11, p. e0166311, 2016.
N. Satabongkoch, S. Khunamornpong, T. Pongsuvareeyakul, J. Settakorn, K. Sukpan, A. Soongkhaw, et al., "Prognostic Value of Tumor Budding in Early-Stage Cervical Adenocarcinomas," Asian Pacific journal of cancer prevention: APJCP, vol. 18, p. 1717, 2017.
Y. H. Lai, L. C. Wu, P. S. Li, W. H. Wu, S. B. Yang, P. Xia, et al., "Tumour budding is a reproducible index for risk stratification of patients with stage II colon cancer," Colorectal Disease, vol. 16, pp. 259-264, 2014.
A. Mezheyeuski, I. Hrynchyk, M. Karlberg, A. Portyanko, L. Egevad, P. Ragnhammar, et al., "Image analysis-derived metrics of histomorphological complexity predicts prognosis and treatment response in stage II-III colon cancer," Scientific reports, vol. 6, p. 36149, 2016.
I. Zlobec, M. Hädrich, H. Dawson, V. Koelzer, M. Borner, M. Mallaev, et al., "Intratumoural budding (ITB) in preoperative biopsies predicts the presence of lymph node and distant metastases in colon and rectal cancer patients," British journal of cancer, vol. 110, p. 1008, 2014.
R. Cappellesso, C. Luchini, N. Veronese, M. L. Mele, E. Rosa-Rizzotto, E. Guido, et al., "Tumor Budding as a Risk Factor for Nodal Metastasis in Pt1 Colorectal Cancers: A Meta-Analysis," Human Pathology, 2017, 65, 62-70.
R. P. Graham, R. A. Vierkant, L. S. Tillmans, A. H. Wang, P. W. Laird, D. J. Weisenberger, et al., "Tumor Budding in Colorectal Carcinoma: Confirmation of Prognostic Significance and Histologic Cutoff in a Population-based Cohort," The American journal of surgical pathology, vol. 39, pp. 1340-1346, 2015.
V. H. Koelzer, I. Zlobec, M. D. Berger, G. Cathomas, H. Dawson, K. Dirschmid, et al., "Tumor budding in colorectal cancer revisited: results of a multicenter interobserver study," Virchows Archiv, vol. 466, pp. 485-493, 2015.
V. H. Koelzer, I. Zlobec, and A. Lugli, "Tumor budding in colorectal cancer—ready for diagnostic practice?"Human pathology, vol. 47, pp. 4-19, 2016.
F. Petrelli, E. Pezzica, M. Cabiddu, A. Coinu, K. Borgonovo, M. Ghilardi, et al., "Tumour budding and survival in stage II colorectal cancer: A systematic review and pooled analysis," Journal of gastrointestinal cancer, vol. 46, pp. 212-218, 2015.
A. Lugli, R. Kirsch, Y. Ajioka, F. Bosman, G. Cathomas, H. Dawson, et al., "Recommendations for reporting tumor budding in colorectal cancer based on the International Tumor Budding Consensus Conference (ITBCC) 2016," Modern Pathology, 2017.
F. Grizzi, G. Celesti, G. Basso, and L. Laghi, "Tumor budding as a potential histopathological biomarker in colorectal cancer: Hype or hope?"World Journal of Gastroenterology: WJG, vol. 18, p. 6532, 2012.
R. L. Siegel, K. D. Miller, S. A. Fedewa, D. J. Ahnen, R. G. Meester, A. Barzi, et al., "Colorectal cancer statistics, 2017," CA: a cancer journal for clinicians, vol. 67, pp. 177-193, 2017.
V. H. Koelzer, N. Assarzadegan, H. Dawson, B. Mitrovic, A. Grin, D. E. Messenger, et al., "Cytokeratin-based assessment of tumour budding in colorectal cancer: Analysis in stage II patients and prospective diagnostic experience" J Path: Clin Res Jul. 2017; 3: 171-178.
G. Rieger, V. H. Koelzer, H. E. Dawson, M. D. Berger, M. Hädrich, D. Inderbitzin, et al., "Comprehensive assessment of tumour budding by cytokeratin staining in colorectal cancer," Histopathology, vol. 70, pp. 1044-1051, 2017.
A. Gordon, G. Glazko, X. Qiu, and A. Yakovlev, "Control of the mean number of false discoveries, Bonferroni and stability of multiple testing," The Annals of Applied Statistics, pp. 179-190, 2007.
E. L. Korn and B. Freidlin, "A note on controlling the number of false positives," Biometrics, vol. 64, pp. 227-231, 2008.
Rogers, A. C., et al. (2016). "Systematic review and meta-analysis of the impact of tumour budding in colorectal cancer." Br J Cancer 115(7): 831-840.
Schneider, N. I. and C. Langner (2014). "PrognosEc straEficaEon of colorectal cancer paEents: current perspecEves." Cancer Manag Res 6: 291-300.
Caie, P. D., et al. (2014). "Quantification of tumour budding, lymphatic vessel density and invasion through image analysis in colorectal cancer." J Transl Med 12: 156.
Kim, J. H., et al. (2015). "Pathologic Factors Associated with Prognosis after Adjuvant Chemotherapy in Stage II/III Microsatellite-Unstable Colorectal Cancers." J Pathol Transl Med 49(2): 118-128.
Rew, D. A., et al. (1991). "Proliferation characteristics of human colorectal carcinomas measured in vivo." Br J Surg 78(1): 60-66.
Klintrup, K., et al. (2005) "Inflammation and prognosis in colorectal cancer." Eur J Cancer 41(17): 2645-2654.
Vayrynen, J. P., et al. (2013). "Detailed analysis of inflammatory cell infiltration in colorectal cancer." Br J Cancer 109(7): 1839-1847.
Mei, Z., et al. (2014). "Tumour-infiltrating inflammation and prognosis in colorectal cancer: systematic review and meta-analysis." Br J Cancer 110(6): 1595-1605.
Richards, C. H., et al. (2012). "Prognostic value of tumour necrosis and host inflammatory responses in colorectal cancer." Br J Surg 99(2): 287-294.
Otsu, A threshold selection method from grey-level histograms, Automatica, vol. 11, pp. 23-27, 1975.

\* cited by examiner

AUTOMATED IDENTIFICATION OF TUMOR BUDS

CROSS REFERENCE TO RELATED APPLICATION

This application claims priority to and benefit of U.S. provisional patent application Ser. No. 62/613,464 filed Jan. 4, 2018, which is fully incorporated by reference and made a part hereof.

FIELD OF THE INVENTION

The present disclosure relates to the detection of tumor buds in tumors and more specifically, to an automated analysis of histology images of sectioned and stained cancer tumors to detect areas of tumor budding.

BACKGROUND

Tumor budding has emerged as an important adverse prognostic factor for increasing number of different cancer types, including colorectal cancer, head and neck squamous cell carcinoma [1, 2], breast cancer [3], esophageal cancer [4], gastric cancer [5, 6], and cervical cancer [7, 8]. In multiple recent studies of colorectal cancer, tumor budding [9-16] has been associated with higher tumor stage, lymph node metastasis, and decreased disease-free survival. Additionally, tumor budding has been included as a reportable feature in the Colorectal Cancer Protocol published by the College of American Pathologists.

Tumor budding is defined as the presence of single tumor cells or small tumor clusters (e.g., up to 5 cells) that "bud" from the invasive front of the main tumor [17]. Tumor budding is believed to represent a type of epithelial-to-mesenchymal transition, in that the tumor cells gained migratory capability by loss of cell-to-cell adhesions and polarity. Thus, tumor budding is the first biologic step towards metastasis. In colorectal carcinoma, for example, tumor budding has been associated with tumors having an aggressive biology. Additionally, tumor budding, in cases of colorectal cancer, has been independently associated with poor treatment outcome, lymph node metastasis, and high recurrence [18]. Because tumor budding has been associated with poor treatment outcomes, identification of tumor budding in colorectal cancers (e.g., via endoscopically-resected malignant polyps) is important at an early stage so that more aggressive management may be pursued.

Assessment of tumor budding (i.e., tumor bud identification) by manual methods requires close evaluation of the tumor invasive front under intermediate to high power (e.g., 200 or 400 times) magnification. This manual assessment, however, is time-consuming and subjective, which could hinder it from becoming a routine procedure in diagnosing and treating common cancers. Colorectal cancer, for example, is the third most common cancer with an estimated incidence in 2017 of over a hundred thousand (i.e., 134,430) new cases in the United States alone [19]. Manual assessments for this large number of cases is challenging and plagued by inter-observer variability. A need, therefore, exists for automating the process of tumor bud identification, not just for evaluation of colorectal cancer, but also for an increasing number of other cancer types.

SUMMARY

Accordingly, the present disclosure embraces an automated image analysis to detect and quantify tumor budding in routine magnified images of sectioned and stained tumors. The results of the tumor budding identification may be used to guide or replace human analysis and/or may be used predict a clinical outcome.

In one aspect, the present disclosure embraces a method for identifying tumor buds in an image of a pan-cytokeratin AE1/3 stained section of a tumor using image processing and analysis. In the method, an image comprised of pixels is received. The image is a magnified view of the stained section of the tumor and is typical of images used for manual histological analysis. The image is segmented to identify the tissues areas within the image. To segment the image, the image is (automatically) thresholded to identify each pixel as either corresponding to a tissue or not corresponding to a tissue (e.g., debris such as a necrotic tissue). Next, the size (e.g., number of pixels) of each tissue area is determined and compared to a lower threshold and an upper threshold to identify candidate areas (i.e., tissue areas likely to contain tumor buds) and eliminate tissue areas that are not likely to contain tumor buds (e.g., fat). Candidate areas are selected as tissue areas that have a size between the upper threshold and the lower threshold. Finally, the cells in each candidate area are counted, and candidate areas that have between one and five cells are (automatically) identified as tumor buds.

In one possible implementation of the method, the thresholding of the image includes converting the image to a gray-scale image (e.g., having pixels values in the range of 0-255) and comparing each pixel's value to a threshold that is computed using Otsu's method, as described in, for example, "*A threshold selection method from gray-level histograms*," (Otsu, Automatica, vol. 11, pp. 23-27, 1975), which is incorporated herein by reference in its entirety. The result of the thresholding includes a binary image that indicates tissue areas (e.g., with a non-zero pixel value) and non-tissue areas (e.g., with a zero pixel value). Accordingly, the tissue areas in the received image can be determined based on the binary image. In some embodiments, morphological operations are applied to the binary image to improve the thresholding process. For example, morphological operations may be applied to the binary image to correct errors (e.g., noise) in the thresholding process. The morphological operations applied may include dilation, filling (i.e., closing), and/or erosion.

In another possible implementation, the pixels within each identified tissue area may be counted to determine the size of each tissue area for comparison with the upper and lower threshold. For example, the lower and upper thresholds may be 16 pixels (e.g., 4 pixels by 4 pixels) and 4096 pixels (e.g., 64 pixels by 64 pixels) respectively. In this way, identified tissue areas smaller than the lower threshold, which likely due to noise and/or imperfect staining, and identified tissue areas larger than the upper threshold, which are likely due to other tissue components (e.g., fat), can be eliminated as candidate areas for analysis.

In another possible implementation, nuclei are assumed as cell proxies for the purposes of counting cells. Accordingly, each candidate area is searched for nuclei, and the detected nuclei in each candidate area are counted to determine the number of cells in each candidate area. As mentioned, candidate regions having one to five cells may be identified as tumor buds. In some cases, no nuclei may be detected in one or more candidate areas. In these cases, additional information may be required to determine if the candidate area is a tumor bud. For example, a shape (e.g., substantially circular) an intensity (e.g., average pixel value above a threshold) of a candidate areas with no nuclei may be used to determine that the candidate area without nuclei is a tumor bud. Additional information may also be determined about candidate areas based on the cell count. For example, candidate areas with more than five nuclei are typically part of the main tumor.

In another possible implementation, the method includes presenting the results of the tumor bud identification. The results may be presented (to a user) in various ways. For example, the received image may be modified to include an indication (e.g., highlighting or circling) of tumor buds in the received image. In another example, a user may be presented with a count of the number of tumor buds contained in the received image and/or a count of the number of cells that each tumor bud contains. In another example, a user may be presented with a relative position of each tumor bud (e.g., a distance of each tumor bud to a tumor front).

In another aspect, the present disclosure embraces a method for identifying tumor buds in a digitized image of an H&E stained section of a tumor (under magnification). In the method, a machine learning classifier is first trained to detect tumor buds using a set of training images H&E of stained sections of tumors with tumor buds. In the training process, the training images are received and textural/spatial features from each training image are extracted and represented as vectors, which are used to train the machine learning classifier. Then, after training, the machine learning classifier is used to identify tumor buds in a received image of an H&E stained section of a tumor (i.e., a tumor that may or may not have tumor buds). After the image is received, the textual and spatial features in the image are extracted and represented as candidate vectors. The candidate vectors are then classified using the trained machine learning classifier to identify tumor buds in the image.

The method may be implemented using a support vector machine or a neural network as the machine learning classifier. Additionally, the textual and spatial features may include local binary patterns, histograms of oriented gradients, or multiresolution Shearlet transforms. Further, in a possible implementation, the training process may include deep learning.

In another aspect, the present disclosure embraces a method for predicting a clinical outcome for a cancer diagnosis or treatment. In the method, a magnified image of a stain section of a tumor is obtained. Tumor buds are then automatically detected in a received image using image analysis (e.g., as in the above methods). The section is then scored based on the detected tumor buds, and a correlation with the clinical outcome is determined through a regression analysis using the score.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

FIGS. 3A-C are images corresponding intermediate steps in the method of FIG. 1, wherein FIG. 3A is a binary image depicting tissue areas corresponding to the image of FIG. 1, FIG. 3B depicts detected nuclei within the tissue areas, and FIG. 3C is a binary image depicting identified tumor buds corresponding to the image of FIG. 1.

DETAILED DESCRIPTION

Recent findings have suggested the use of pan-cytokeratin (AE1/3) immunostaining for the evaluation of tumor budding is feasible in daily diagnostic practice [20]. A study by the Swiss Association of Gastrointestinal Pathology in 2016 found that tumor budding counts are three to six times greater upon pan-cytokeratin staining compared to the standard H&E staining. The same study also found that interobserver reproducibility was markedly improved with pan-cytokeratin staining compared to H&E. Koelzer [20] and Rieger et al. [21][8] presented a comprehensive assessment of tumor budding by cytokeratin staining in colorectal cancer. Koelzer [20] also concluded that assessment of tumor budding on pan-cytokeratin slides is feasible in a large pathology institute and leads to expected associations with clinic-pathological features. AE1/3 specifically highlights tumor cells while de-emphasizing normal cells, making it very useful in computer assisted tumor budding assessment.

Tumor Bud Identification in Pan-Cytokeratin AE1/3 Images

Figure 1:
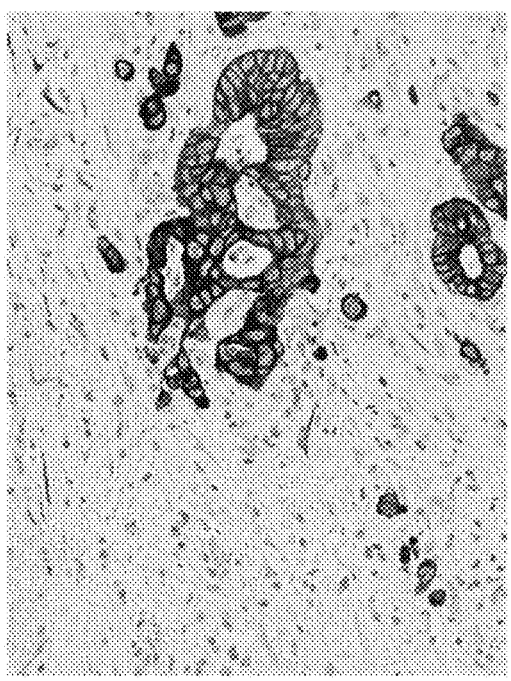
FIG. 1 is an example image of a pan-cytokeratin AE1/3 stained section of a tumor under magnification.
Figure 2:
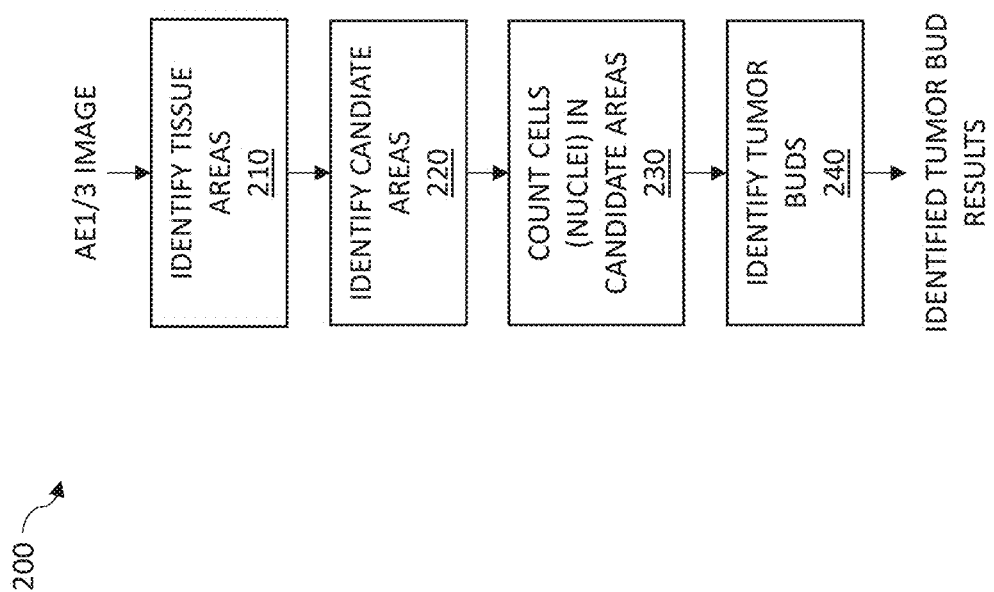
FIG. 2 is a flow chart depicting an exemplary method for identifying tumor buds in an image of a pan-cytokeratin AE1/3 stained section of a tumor.

An image of a pan-cytokeratin AE1/3 stained section of a tumor is shown in FIG. 1. As shown, the cytoplasm of cells is stained brown (dark), nuclei are counterstained blue (light), and a background region is white. A method 200 for identifying tumor buds in the image (FIG. 1) generally consists of the operations of tissue segmentation to identify tissue areas 210, filtering the identified tissue areas by size to identify candidate areas 220, counting nuclei (i.e., cells) in the candidate areas 230, and identifying tumor buds based on the number of cells in the candidate areas 240.

Tissue segmentation to identify tissue areas may use thresholding to distinguish nuclei tissue from the background and from debris (e.g., necrotic tissues). Additionally, noise and small spurious segments from debris may be removed in the segmentation process. This removal is especially important when debris or necrotic tissues are present in the image. This noise removal may use an adjustable threshold, but care should be taken that it is not selected too large because potential tumor buds may be removed.

Segmentation may use an automatic thresholding in which the threshold is computed using Otsu's method. In a typical embodiment, initial parameters are provided to an Otsu thresholding algorithm. The initial parameters provided to the Otsu thresholding algorithm may include an Otsu threshold of t=64 pixels and an Otsu weight w=1.25. These parameters may be selected optimally as a study requires.

Additionally, identifying tissue areas 200 may require morphological operations (e.g., dilation, filling, and erosion) to correct for thresholding errors and provide the identification of tissue areas.

Figure 3A:
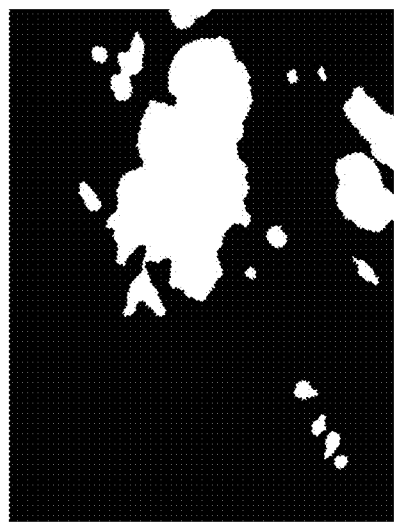

FIG. 3A illustrates the results of tissue segmentation (i.e., identification of tissue areas) for the image of FIG. 1. As shown, the results include a binary image, wherein pixels corresponding to tissues area white and pixels not corresponding to tissue (e.g., debris, background, etc.) are black.

This binary image may be used to determine the areas in the image (FIG. 1) that correspond to tissues.

The tissue areas may be filtered in terms of size to identify candidate areas likely to contain tumor buds (i.e., candidate areas). The size of each candidate areas should not be too small or too large. Accordingly, two threshold values $n_1$ and $n_2$ are used to identify candidate areas from the tissue areas. Regions smaller than $n_1$ are likely to be noise (e.g., due to imperfect staining), while regions larger than $n_2$ are likely to be another tissue component (e.g., fat). In a typical implementation, thresholds of $n_1$=16 and $n_2$=4096 pixels may be used to identify the candidate areas from the tissue areas. In the example shown in FIG. 3A, the tissue areas are all identified as candidate areas. These threshold values may be optimized based on the application.

Figure 3B:
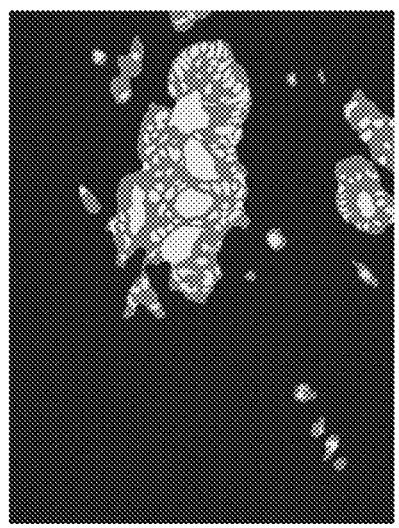

To identify tumor buds, cells within each candidate area may be counted and compared to a range. Because nuclei indicate a cell, nuclei detection forms the basis of cell counting. FIG. 3B shows the candidate areas of FIG. 3A with detected nuclei (shown as light gray).

As mentioned previously, AE1/3 staining highlights the tumor budding cells while de-emphasizing non-epithelial cells, hence the detected nuclei from the operations of segmentation and nuclei detection are all tumor cells. After nuclei detection, cell counting (i.e., nuclei counting) within the candidate areas is performed and candidate areas with a cell count in a range of one to five cells may be identified as tumor buds. Additionally, tissue segments with more than five cells may be identified as part of the main tumor. The number of nuclei used to identify a tumor bud may be optimized based on the application.

Tissue cells with no visible nuclei are not immediately classified tumor buds but are considered exceptions that require further analysis. Accordingly, tissue segments with no detected cells (i.e., nuclei), can be further analyzed in terms of a shape and intensity of the tissue. For example, tissue regions having no visible nuclei that also have a high average intensity and a high degree of circularity may be identified as tumor buds.

Figure 3C:
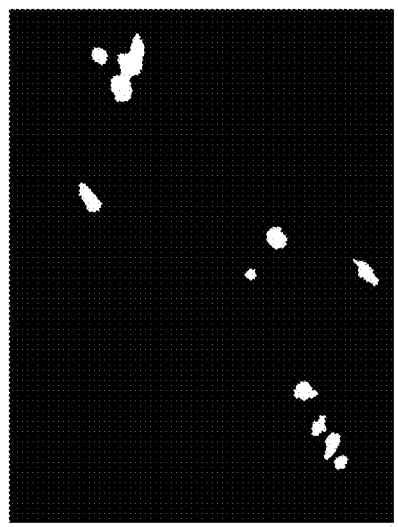

FIG. 3C illustrates the tumor buds identified from an analysis of FIG. 3B. The tumor buds are candidate areas that meet the cell count and size/shape criteria described above. Using this binary image of tumor buds, results may be generated and presented.

Figure 4:
FIG. 4 illustrates exemplary results of tumor bud identification, wherein the image of FIG. 1 is shown with indications of identified tumor buds.
Figure 5:
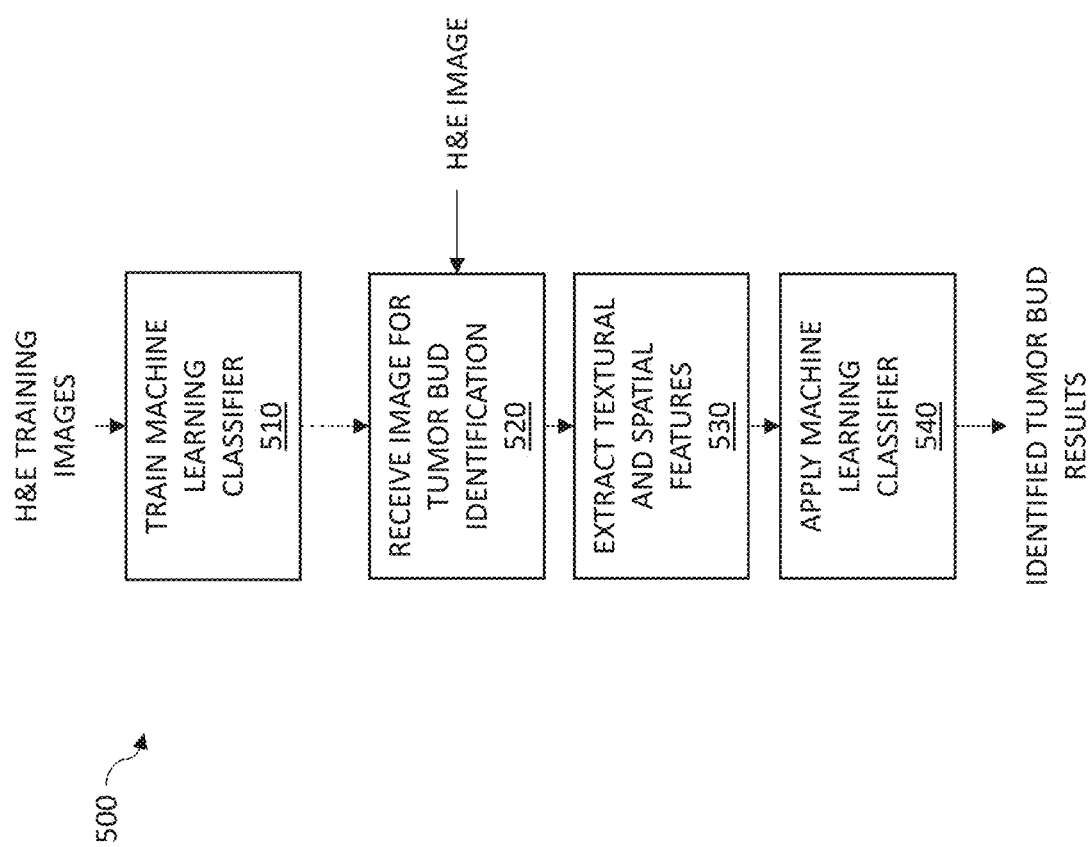
FIG. 5 is a flowchart depicting an exemplary method for identifying tumor buds in an image of an H&E stained section of a tumor.

FIG. 4 illustrates the image of FIG. 1 with indications of tumor buds. Additional results may also be generated. The results may include a count of the number of tumor buds and the relative location of tumor buds. The results may be presented to a user and may guide the user in a visual analysis of the tumor section. Further, in some cases, the results may replace a manual analysis of the image (or slide) by a human.

While AE1/3 staining facilitates tumor budding evaluation, it is not used routinely in evaluating colorectal cancer. College of American Pathologists Cancer Protocol and International Tumor Budding Consensus Conference (ITBCC, 2016) recommend the following [17]:

"Tumor budding counts should be done on H&E sections. In cases of obscuring factors like inflammation, immunohistochemistry for keratin can be obtained to assess the advancing edge for tumor buds, but the scoring should be done on H&E sections."

Accordingly, the present disclosure also embraces a method for detecting tumor buds in images of hematoxylin and eosin (H&E) stained slides.

Tumor Bud Identification in Hematoxylin and Eosin (H&E) Images

A relative distribution of normalized color features can be used to identify tumor bud regions with high sensitivity and relatively low specificity. The identification method 500 consists of initially training 510 a machine learning classifier to classify textural and spatial features that correspond to tumor buds in a set of training images. Each training image is a magnified image of an H&E stained section of a tumor with tumor buds. After the machine learning classifier is trained, the machine learning classifier may be applied 540 to determine if textural and spatial features extracted 530, from an image received 520 for tumor bud identification, correspond to tumor buds.

In the method, color deconvolution is first applied to separate the hematoxylin from the eosin images. Textural and spatial features (i.e., represented as quantitative vectors) are then be extracted and input to the machine learning classifier (e.g., a support vector machine or a neural network) to detect tumor bud regions. Local binary patterns (LBP), histogram of oriented gradients (HOG) and the multiresolution Shearlet transform (i.e., an extension of wavelet transform) are among the suitable techniques to be used to extract textural and shape features from the histology images. Deep learning approach may also be used depending on the number of training images available. For example, if the number of training samples are small deep learning may not provide optimal results. In some implementations, the candidate regions are further refined by analyzing the area and distance of the regions to the tumor front.

Results from an Example Implementation of the Method for Identifying Tumor Buds in AE1/3 Images Fifteen cases from Ohio Colorectal Cancer Prevention Initiative (OCCPI) cohort have been identified for digital image analysis, double stained with both AE1/3 and H&E. High power field images (40× magnification) with varying number of tumor buds (minimum 1 tumor bud region and maximum up to 20 tumor bud regions) have been captured. Five HPF images with comprehensive ground truths are selected, each from three of the 15 AE1/3 cases. Each case corresponds to high power field image at 400 times magnification, with varying number of tumor buds (i.e., minimum 1 tumor bud region and maximum up to 18 tumor bud regions). The ground truth for each case was provided by the collaborating pathologists. The ground truth was annotated by cross-marking with their corresponding H&E images. Table 1 shows the detail summary of the experimental results.

TABLE 1

Summary of Experimental Results

| Images | # TB | TP | FN | FP |
| --- | --- | --- | --- | --- |
| Img01 | 5 | 5 | 0 | 2 |
| Img02 | 1 | 1 | 0 | 0 |
| Img03 | 5 | 4 | 1 | 2 |
| Img04 | 2 | 2 | 0 | 0 |
| Img05 | 2 | 2 | 0 | 0 |
| Img06 | 4 | 3 | 1 | 0 |
| Img07 | 6 | 6 | 0 | 4 |
| Img08 | 2 | 2 | 0 | 2 |

TABLE 1-continued

Summary of Experimental Results

| Images | # TB | TP | FN | FP |
|---|---|---|---|---|
| Img09 | 5 | 5 | 0 | 0 |
| Img10 | 18 | 17 | 1 | 4 |
| Img11 | 7 | 6 | 1 | 0 |
| Img12 | 5 | 4 | 1 | 0 |
| Img13 | 5 | 5 | 0 | 0 |
| Img14 | 6 | 5 | 1 | 0 |
| Img15 | 8 | 8 | 0 | 0 |
| Total | 81 | 75 | 6 | 14 |

The first column in Table 1 lists the ID of the HPF cases, the second column shows the total number of tumor budding regions marked by the pathologists, while columns three to five shows the true positive (TP), false negative (FN), and false positive (FP) of the proposed tumor bud detection system.

From the results, a sensitivity of 92.6% and specificity of 84.3% may be computed for ground truth. These results demonstrate the reliability of the proposed automated system.

The techniques disclosed may reveal associations and correlations with a variety of clinically relevant outcomes. Accordingly, it is envisioned that classification and clustering tools (heatmaps, etc.) may be used for this purpose.

Tumor recurrence, tumor progression, and the association with selected features/clinical covariates and or groups of features may be modeled using logistic regression or Cox regression models (with random subject effects). Associations between a time to recurrence and a progression of different features or feature clusters may be revealed using Cox regression models.

Predictive models can be developed for time to recurrence and time to progression. For example, predictive models may be developed through a stepwise approach using a Bayesian information criterion (BIC) or an Akaike information criterion (AIC). Alternatively, predictive models may be developed using a K-fold or a penalized likelihood approach.

Logistic regression models can be used to study association with tumor budding scores. Because the number of features is often large compared to the number of samples, feature selection methods can be utilized to control the number of false positives. The significance level can be adjusted by controlling the mean number of false positives [22, 23].

Multivariate prediction models, using features identified by above analyses, can be developed incorporating important covariates, such as age, race, tumor characteristics, or other known prognostic factors. To overcome the overfitting problem with a large number of features penalized likelihood maximization (e.g., least absolute shrinkage and selection operator (LASSO)) and penalized risk minimization approaches can be used together with cross-validation methods for building prediction models of clinical outcomes.

In the specification and/or figures, typical embodiments have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

REFERENCES

[1] M. Boxberg, M. Jesinghaus, C. Dorfner, C. Mogler, E. Drecoll, A. Warth, et al., "Tumour budding activity and cell nest size determine patient outcome in oral squamous cell carcinoma: proposal for an adjusted grading system," Histopathology, vol. 70, pp. 1125-1137, 2017.

[2] P. V. Angadi, P. V. Patil, K. Hallikeri, M. Mallapur, S. Hallikerimath, and A. D. Kale, "Tumor budding is an independent prognostic factor for prediction of lymph node metastasis in oral squamous cell carcinoma," International journal of surgical pathology, vol. 23, pp. 102-110, 2015.

[3] X. Li, B. Wei, C. Sonmez, Z. Li, and L. Peng, "High tumor budding count is associated with adverse clinicopathologic features and poor prognosis in breast carcinoma," Human Pathology, 2017.

[4] M. Jesinghaus, M. Boxberg, B. Konukiewitz, J. Slotta-Huspenina, A. M. Schlitter, K. Steiger, et al., "A Novel Grading System Based on Tumor Budding and Cell Nest Size Is a Strong Predictor of Patient Outcome in Esophageal Squamous Cell Carcinoma," The American Journal of Surgical Pathology, vol. 41, pp. 1112-1120, 2017.

[5] K. Che, Y. Zhao, X. Qu, Z. Pang, Y. Ni, T. Zhang, et al., "Prognostic significance of tumor budding and single cell invasion in gastric adenocarcinoma," OncoTargets and therapy, vol. 10, p. 1039, 2017.

[6] S. Olsen, J. Linda, R. C. Fields, Y. Yan, and I. Nalbantoglu, "Tumor Budding in Intestinal Type Gastric Adenocarcinoma is Associated with Nodal Metastasis and Recurrence," Human Pathology, 2017.

[7] B. Huang, J. Cai, X. Xu, S. Guo, and Z. Wang, "High-Grade Tumor Budding Stratifies Early-Stage Cervical Cancer with Recurrence Risk," PloS one, vol. 11, p. e0166311, 2016.

[8] N. Satabongkoch, S. Khunamornpong, T. Pongsuvareeyakul, J. Settakorn, K. Sukpan, A. Soongkhaw, et al., "Prognostic Value of Tumor Budding in Early-Stage Cervical Adenocarcinomas," Asian Pacific journal of cancer prevention: APJCP, vol. 18, p. 1717, 2017.

[9] Y. H. Lai, L. C. Wu, P. S. Li, W. H. Wu, S. B. Yang, P. Xia, et al., "Tumour budding is a reproducible index for risk stratification of patients with stage II colon cancer," Colorectal Disease, vol. 16, pp. 259-264, 2014.

[10] A. Mezheyeuski, I. Hrynchyk, M. Karlberg, A. Portyanko, L. Egevad, P. Ragnhammar, et al., "Image analysis-derived metrics of histomorphological complexity predicts prognosis and treatment response in stage II-III colon cancer," Scientific reports, vol. 6, p. 36149, 2016.

[11] I. Zlobec, M. Hadrich, H. Dawson, V. Koelzer, M. Borner, M. Mallaev, et al., "Intratumoural budding (ITB) in preoperative biopsies predicts the presence of lymph node and distant metastases in colon and rectal cancer patients," British journal of cancer, vol. 110, p. 1008, 2014.

[12] R. Cappellesso, C. Luchini, N. Veronese, M. L. Mele, E. Rosa-Rizzotto, E. Guido, et al., "Tumor Budding as a Risk Factor for Nodal Metastasis in Pt1 Colorectal Cancers: A Meta-Analysis," Human Pathology, 2017.

[13] R. P. Graham, R. A. Vierkant, L. S. Tillmans, A. H. Wang, P. W. Laird, D. J. Weisenberger, et al., "Tumor Budding in Colorectal Carcinoma: Confirmation of Prognostic Significance and Histologic Cutoff in a Population-based Cohort," The American journal of surgical pathology, vol. 39, pp. 1340-1346, 2015.

[14] V. H. Koelzer, I. Zlobec, M. D. Berger, G. Cathomas, H. Dawson, K. Dirschmid, et al., "Tumor budding in colorectal cancer revisited: results of a multicenter interobserver study," Virchows Archiv, vol. 466, pp. 485-493, 2015.

[15] V. H. Koelzer, I. Zlobec, and A. Lugli, "Tumor budding in colorectal cancer—ready for diagnostic practice," Human pathology, vol. 47, pp. 4-19, 2016.

[16] F. Petrelli, E. Pezzica, M. Cabiddu, A. Coinu, K. Borgonovo, M. Ghilardi, et al., "Tumour budding and survival in stage II colorectal cancer: A systematic review and pooled analysis," Journal of gastrointestinal cancer, vol. 46, pp. 212-218, 2015.

[17] A. Lugli, R. Kirsch, Y. Ajioka, F. Bosman, G. Cathomas, H. Dawson, et al., "Recommendations for reporting tumor budding in colorectal cancer based on the International Tumor Budding Consensus Conference (ITBCC) 2016," Modern Pathology, 2017.

[18] F. Grizzi, G. Celesti, G. Basso, and L. Laghi, "Tumor budding as a potential histopathological biomarker in colorectal cancer: Hype or hope?," World Journal of Gastroenterology: WJG, vol. 18, p. 6532, 2012.

[19] R. L. Siegel, K. D. Miller, S. A. Fedewa, D. J. Ahnen, R. G. Meester, A. Barzi, et al., "Colorectal cancer statistics, 2017," CA: a cancer journal for clinicians, vol. 67, pp. 177-193, 2017.

[20] V. H. Koelzer, N. Assarzadegan, H. Dawson, B. Mitrovic, A. Grin, D. E. Messenger, et al., "Cytokeratin-based assessment of tumour budding in colorectal cancer: Analysis in stage II patients and prospective diagnostic experience," The Journal of Pathology: Clinical Research.

[21] G. Rieger, V. H. Koelzer, H. E. Dawson, M. D. Berger, M. Hädrich, D. Inderbitzin, et al., "Comprehensive assessment of tumour budding by cytokeratin staining in colorectal cancer," Histopathology, vol. 70, pp. 1044-1051, 2017.

[22] A. Gordon, G. Glazko, X. Qiu, and A. Yakovlev, "Control of the mean number of false discoveries, Bonferroni and stability of multiple testing," The Annals of Applied Statistics, pp. 179-190, 2007.

[23] E. L. Korn and B. Freidlin, "A note on controlling the number of false positives," Biometrics, vol. 64, pp. 227-231, 2008.

The invention claimed is:

1. A method for identifying tumor buds in an image of a section of a tumor stained only with a immunohistochemical stain for pan-cytokeratin AE1/3, the method comprising:
receiving the image, wherein the image is a magnified view of the section of the tumor stained only with the immunohistochemical stain for pan-cytokeratin AE1/3 and is comprised of pixels;
segmenting the image to identify tissue areas, wherein the segmenting comprises thresholding the image to identify each pixel as corresponding to tissue or as not corresponding to tissue;
determining a size of each identified tissue area;
comparing the size of each identified tissue area to a lower threshold and an upper threshold to identify candidate areas in the image as tissue areas that have a size between the upper threshold and the lower threshold; and
counting the number of cells in each candidate area of the image, wherein counting the number of cells comprises detecting nuclei in the candidate areas and counting nuclei in each candidate area to determine the number of cells in each candidate area;
identifying candidate areas with nuclei;
analyzing a shape and an intensity of the candidate areas with nuclei; and
determining that the candidate area with nuclei is a tumor bud based the candidate area having between one and five cells and candidate area's shape and intensity.

2. The method according to claim 1, wherein the thresholding of the image to identify each pixel as corresponding to a tissue or as not corresponding to a tissue comprises:
converting the image to a gray-scale image; and
comparing each pixel's value to a threshold that is computed using Otsu's method;
creating a binary image that indicates tissue areas based on the comparison; and
determining areas in the image corresponding to tissues based on the binary image.

3. The method according to claim 2, wherein the thresholding of the image to identify each pixel as corresponding to a tissue or as not corresponding to a tissue further comprises:
applying, after creating the binary image, morphological operations to the binary image.

4. The method according to claim 3, wherein the morphological operations comprise one or more of a dilation, a filling, and an erosion.

5. The method according to claim 1, wherein determining a size of each identified tissue area comprises: counting a number of pixels within in each identified tissue area.

6. The method according to claim 5, wherein the lower threshold is 16 pixels and the upper threshold is 4096 pixels.

7. The method according to claim 1, wherein the comparing the size of each identified tissue area to a lower threshold and an upper threshold to identify candidate areas in the image as tissue areas that have a size between the upper threshold and the lower threshold further comprises:
determining that an identified tissue area having a size smaller than the lower threshold is noise caused by errors in the sectioning or staining of the tumor; and eliminating the noise from the candidate areas.

8. The method according to claim 1, wherein the comparing the size of each identified tissue area to a lower threshold and an upper threshold to identify candidate areas in the image as tissue areas that have a size between the upper threshold and the lower threshold further comprises:
determining that an identified tissue area having a size larger than the upper threshold is fat; and eliminating the fat from the candidate areas.

9. The method according to claim 1, further comprising:
identifying a candidate area that has more than five nuclei as part of a main tumor.

10. The method according to claim 1, further comprising:
presenting results of the identified tumor buds, wherein the results comprise one or more of:
an indication of each tumor bud in the image, and
a count of the number of tumor buds.

11. The method of claim 10, wherein presenting results of the identified tumor buds further comprises presenting a distance of each identified tumor bud to a tumor front.

* * * * *